United States Patent [19]

Young et al.

[11] 4,190,680

[45] Feb. 26, 1980

[54] ADHERENT CONTROLLED RELEASE PESTICIDES

[75] Inventors: Robert W. Young, New York, N.Y.; Samuel Prussin, Carmel, Calif.; Norman G. Gaylord, New Providence, N.J.

[73] Assignee: Young, Prussin, Mgk, J. V., New York, N.Y.

[21] Appl. No.: 933,515

[22] Filed: Aug. 14, 1978

Related U.S. Application Data

[63] Continuation of Ser. No. 868,685, Jan. 11, 1978, abandoned, which is a continuation of Ser. No. 696,360, Jun. 15, 1976, abandoned.

[51] Int. Cl.$^2$ ............................................. A61K 31/00
[52] U.S. Cl. .................................... 427/4; 71/DIG. 1; 424/DIG. 10; 424/167; 424/127; 424/186; 427/2; 424/78
[58] Field of Search ................ 71/DIG. 1; 260/429.5, 260/429.7; 424/184, 182, 19, 178, 71, DIG. 10, DIG. 6, 166, 127; 427/4, 2; 43/136

[56] References Cited

U.S. PATENT DOCUMENTS

| | | | |
|---|---|---|---|
| 2,681,878 | 6/1954 | Kauppi | 424/184 |
| 2,923,095 | 2/1960 | Pellonnier | 427/4 |
| 3,151,969 | 10/1964 | Stevens | 424/186 |
| 3,480,653 | 11/1969 | Pande | 260/429.5 X |
| 3,779,932 | 12/1973 | Jagger et al. | 260/429.5 |
| 3,836,647 | 9/1974 | Lange | 424/184 |
| 3,886,125 | 5/1975 | Chromecek | 71/DIG. 1 X |

Primary Examiner—Sam Silverberg
Attorney, Agent, or Firm—Roylance, Abrams, Berdo & Farley

[57] ABSTRACT

There are disclosed methods and compositions for the controlled release of insecticides by using a mixture consisting of (a) a hydrolyzable organic titanium compound or a partial hydrolyzate thereof, and (b) a pesticide, e.g., an insecticide.

11 Claims, No Drawings

ADHERENT CONTROLLED RELEASE PESTICIDES

This is a continuation of application Ser. No. 868,685 filed Jan. 11, 1978 now abandoned which is a continuation of application Ser. No. 696,360, filed June 15, 1976 now abandoned.

This invention relates to methods and compositions for the controlled release of bioactive agents and, more particularly, to the controlled release of pesticides, such as insecticides.

The utilization of bioactive agents such as pesticides, e.g., insecticides, herbicides and fungicides has become an important fact of life. However, these materials are generally effective only as long as they persist on the substrate to which they are applied.

The basic motivation underlying the modern development of controlled release pesticidal materials has been to extend the duration between applications and thus increase the efficiency and hence economy of control. Controlled release of pesticides permits extended time intervals between treatments and reduction of the dosage, thus reducing environmental impact. Thus, from an ecological standpoint, controlled release of pesticides enhances the lifetime of a non-persistent agent at the site of treatment while maintaining the preferred property of rapid detoxification in the environment surrounding the controlled release pesticide.

The desired controlled release of pesticides has previously been achieved by their incorporation within a polymeric matrix, e.g., encapsulation wherein a pest control agent is surrounded by an enveloping polymeric wall that permits loss through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment. However, the prior art approaches fall short of the desired goal in that there is not adequate provision for the adhesion of the pesticide within the polymeric matrix to the substrate. This permits the removal or transfer of the material from the substrate as a result of physical contact, wind, rain or other atmospheric conditions.

One object of the present invention is to provide a process for the controlled release of bioactive agents such as pesticides.

Another object of the present invention is to improve the adhesion of such an agent to suitable substrates and thus to increase its effective lifetime.

Another object of the present invention is to provide stable compositions which after application to a suitable substrate and exposure to the atmosphere, undergo in situ chemical reaction resulting in adherent insecticides with controlled release characteristics.

A further object of the present invention is to provide novel compositions containing reactive, moisture curable, adhesion promoting, organic titanium compounds and insecticides.

These and other objects of the present invention are achieved by using a mixure consisting of (a) a hydrolyzable organic titanium compound or a partial hydrolyzate thereof, and (b) an insecticide.

The hydrolyzable titanium compounds which are suitable for use in the practice of the present invention are the tetraesters, tetraanhydrides and tetraamides of orthotitanic acid.

The titanium tetraesters have the formula:

$$Ti(OR)_4$$

where R is an aliphatic hydrocarbon radical of less than about 20 carbon atoms and may be saturated or unsaturated and acyclic or cyclic. Thus, R may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. Titanium orthoesters where R is the same or mixed are suitable for use in the present invention. Partially hydrolyzed orthoesters may also be used if the hydrolysis has not rendered them insoluble in organic solvents and they still retain alkoxy groups.

The titanium tetraanhydrides have the formula:

$$Ti(OCOR')_4$$

where R' is an aliphatic hydrocarbon radical of less than about 20 carbon atoms and may be saturated or unsaturated and acyclic or cyclic. Thus, R' may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. The anhydrides or acylates may also be prepared from aliphatic acids which contain more than one carboxyl group, such as maleic acid, fumaric acid, etc. Titanium acylates where R' is the same or mixed are suitable for use in the present invention. Mixed alkoxytitanium acylates are also useful. These are prepared by the reaction of a tetraester with an acid or anhydride or of a tetraanhydride with an alcohol under anhydrous conditions. Partially hydrolyzed acylates may also be used.

The titanium tetraamides have the formula:

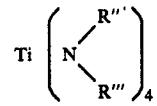

where R" is hydrogen, alkyl or aryl and R''' is alkyl or aryl. The alkyl groups may be saturated or unsaturated and acyclic or cyclic and include methyl, ethyl, propyl, butyl, amyl, octyl, stearyl, oleyl, etc. groups.

The titanium polymers prepared by partial hydrolysis of the monomeric titanium orthoesters, acylates and amides, per se or in admixture, as well as by partial hydrolysis of mixed orthoesters, acylates and amides may also be used in the practice of the present invention.

While hydrolyzability is a general characteristic of the tetraesters, tetraanhydrides and tetraamides of orthotitanic acid which may be used in the practice of the present invention, the rate of hydrolysis is a function of the nature of the hydrocarbon substituent. Thus, the presence of methyl, ethyl and other lower alkyl substituents results in rapid hydrolysis while higher alkyl substituents result in slower hydrolysis. In the latter case it is possible to use water as a diluent or dispersing medium during the preparation and handling of the active compositions, and as the hydrolyzing reactant as the composition is applied or after it is applied to the substrate.

An alternative approach to delayed hydrolysis is the use of an organic titanium chelate. The chelates which are suitable for use in the practice of the present invention are either water soluble or solvent soluble and hydrolyze slowly in aqueous systems per se or when the pH is changed or the temperature is raised.

The titanium chelates are derivatives of bi- or multifunctional compounds in which one of the functional groups is usually hydroxyl or enolic carbonyl and the other group is hydroxyl, carboxyl, carbonyl or amino. Thus, the titanium chelates are derivatives of glycols, hydroxy acids, dicarboxylic acids, diketones, ketoesters or alkanolamines. Representative chelates include chelates of 2-methylpentane-2,4-diol, 2-ethylhexane-1,3-diol, 2-methylpentane-1,3-diol, 2-propylheptane-1,3-diol, lactic acid, glycolic acid, citric acid, tartaric acid, hydroxystearic acid, oxalic acid, acetylacetone, ethyl acetoacetate, diethanolamine, triethanolamine and the like.

The titanium chelates are generally prepared by the reaction of a titanium alkoxide such as tetraisopropyl titanate and the appropriate bi- or multifunctional compound. The preparation and properties of the titanium chelates are disclosed in Kirk-Othmer Encyclopedia of Chemical Technology, John Wiley & Sons, New York, 2nd Edition, Volume 20, pages 464–468 (1969). The preparation of aqueous solutions of the titanium chelates is described in "Tyzor Organic Titanates," E. I. duPont de Nemours & Co., Organic Chemicals Department, Technical Bulletin D-5258. The disclosures of each of the hereinabove identified references are incorporated herein by reference.

The use of organic titanates to modify solid surfaces for the purpose of improving adhesion is well known art. The titanates are generally applied to the solid surface, such as that of glass, metals and polymers, and permitted to hydrolyze to form a primed surface for the subsequent application of films and coatings (U.S. Pat. Nos. 2,768,909 and 2,838,418).

It is surprising, in view of the disclosures of the prior art, that an insecticide can be incorporated into a reactive system, containing an organic titanium compound, and the resultant composition, upon application a suitable surface and reaction with moisture at ambient temperature, provide an adherent, controlled release insecticide.

Insecticides which may be used in the practice of this invention include any of the compounds well known in the art for use as insecticides such as those set forth in Chemical Week, June 21, 1972, pages 39–64; Chemical Week, July 26, 1972, pages 19–41; and Commercial and Experimental Organic Insecticides (1974 Revision), Entomological Society of America, Special Publication 74-1, October 1974. Some common insecticides which may be used include the following:

| | |
|---|---|
| 1-naphthyl methylcarbamate (SEVIN) | pyrethrins |
| malathion | parathion |
| methylparathion | phorate |
| toxaphene | chlordane |
| Dursban | Baygon |
| DDT | Diazinon |

The insecticides which may be used in the practice of this invention also include bacterial insecticides such as *Bacillus popilliae* and *Bacillus thuringiensis* and viral insecticides such as the Heliothis virus. These have been described in Chemical & Engineering News, 35, No. 30, 18 (July 28, 1975), the disclosures of which are incorporated herein by reference.

The insecticide is included in the composition in an amount sufficient to exert an insecticidal action on the immediate environment surrounding the substrate. The amount of insecticide will be dependent upon several factors such as the composition and thickness of the cured polymeric matrix, the nature of the insecticide, i.e., liquid or solid, the presence of active hydrogen functionality, the duration of insecticidal action desired, etc. The optimum amount of insecticide to be included may readily be determined by those skilled in the art. Generally, from about 1 part by weight of insecticide to 0.5 to 1000 parts by weight of the titanium compound is satisfactory.

The compositions of this invention may include volatile diluents such as aliphatic or aromatic hydrocarbons, e.g., Stoddard Solvent, mineral spirits, B&P naphtha, cyclohexane, petroleum ether, benzene, toluene, xylene, etc., halogenated hydrocarbons such as perchloroethylene and fluorocarbons, volatile fluid polysiloxanes such as dimethylpolysiloxane fluids, or alkanols. The compositions may be prepared by merely admixing the various components. Before admixing, the components may be dispersed or dissolved in a diluent such as previously described. The compositions may also be prepared in aqueous media when slowly hydrolyzing and/or stable components are present.

The compositions of this invention may be applied to a large number of substrates. The substrate should be one which contains active hydrogen atoms which provide sites for coupling with the hydrolyzed titanium compound, e.g., hydroxyl groups, amino groups, etc. Thus, various plants such as ornamental bushes, trees, flowers, greenhouse plants, lawns, crops (e.g., wheat, corn, soy beans, barley, oats, cotton, jute, sisle), fruits, vegetables, berry bushes, nut trees, olive trees, fig trees, grape vines; various animals such as household pets (e.g., cats, dogs), farm animals such as dairy cattle, beef cattle, horses, sheep, chickens, turkeys, swine, goats, zoo animals, etc. Non-plant and animal uses include spraying surfaces of structures such as buildings and various rooms in buildings, such as kitchens, bathrooms, closets including wood or plaster board walls and floor tile to protect against roaches, termites, flying insects, rug insects, ants, etc. Various containers such as bags and cardboard or wooden boxes may also serve as substrates in accordance with the practice of this invention.

The compositions of this invention may be applied to the substrate by brushing, spraying, dipping or any other known technique for applying a fluid composition to a solid substrate. It may be applied in the form of an aerosol mist or fog, propelled by conventional pressurized volatile halohydrocarbon, hydrocarbon or compressed gas propellants, an air propelled mist blower, a fog generator, or other suitable means.

Although this invention should not be limited thereby, it is believed that upon application of the compositions of this invention to a suitable substrate in an ambient atmosphere, evaporation of the volatile diluent, if any is present, and exposure to atmospheric moisture results in the hydrolysis of the titanium compound, followed by condensation of the TiOH groups generated thereby. This converts the titanium compound into a higher molecular weight, crosslinked, polymer containing entrapped or occluded insecticide. Simultaneously, the hydrolyzed titanium compound promotes the adhesion of the polymer and the insecticide entrapped or occluded therein to the substrate. Adhesion to the substrate is due at least in part to the fact that the polymeric matrix is coupled to the substrate by reaction through active hydrogen atoms on the substrate. In this manner, the insecticide is held on the substrate to such an extent that it cannot be physically brushed off, blown off or washed off by rain. Further, as a result of its entrapped condition the rapid evaporation, sublimation or extraction of the insecticide is retarded. However, due to the permeability of the polymer to organic compounds, said evaporation or sublimation is not completely inhibited, resulting in controlled release of the insecticide.

When water is present in the compositions of this invention, said water is generally added shortly before application of the composition to a suitable substrate, and hydrolysis of the titanium compound may begin before or during application to said substrate. However, hydrolysis continues after said application and is followed by condensation of the TiOH groups generated thereby.

When a water stable titanium compound, e.g., an organic titanium chelate such as the lactic acid chelate or the triethanolamine chelate, is present, the aqueous composition may be prepared long before application to the substrate. However, an acid or acid-generating compound is added to the aqueous composition shortly before application to the substrate. The resultant lowering of the pH promotes hydrolysis of the titanium compound, which may begin before or during application to the substrate. However, hydrolysis continues after said application and is followed by condensation of the TiOH groups generated thereby.

The rate of release of the insecticide may be controlled by adjusting the extent of crosslinking, e.g., by adjusting the thickness of the polytitanoxane coating, e.g., by modifying the composition and ratio of components in the composition, or by adding a non-volatile, non-reactive extender for the crosslinked polytitanoxane. The latter may be a hydrocarbon oil and acts in a manner analogous to the behavior of the hydrocarbon oil in a vulcanized oil-extended hydrocarbon rubber. The extender may be a compatible non-siloxane compound e.g., a hydrocarbon oil or may be an alkyl or arylpolysiloxane fluid having a viscosity ranging from 5 to 100,000 centistrokes at 25° C.

In addition to or in lieu of the solvents which function to reduce the viscosity of the compositions of this invention as well as control the thickness of the polymeric coating, volatile alcohols such as ethanol, isopropanol, butanol and the like may be included in the composition to prevent premature hydrolysis of the hydrolyzable crosslinking agent with resultant gelation and precipitation.

Other additives which may be incorporated into the compositions of this invention include stabilizers against environmental degradation, such as antioxidants and ultraviolet stabilizers, odor masking compounds and perfumes, dyes, pigments, fillers, etc.

The following examples illustrate the best mode for carrying out this invention. Example I illustrates the improved adhesion of the compositions of this invention to a substrate. In the tables, the numbers refer to the amount of material in parts by weight.

EXAMPLE I

Solutions containing 50 weight-% of tetraisopropyl titanate (TPT) and/or a dimethylpolysiloxane fluid, designated as a DC-200 fluid by the Dow Corning Corp., having a viscosity of 1000 centistokes at 25° C. (DC-200/1000), were prepared in anhydrous isooctane.

The 50% solution was diluted to 10 weight-% with isooctane and 10–20 drops were placed on a weighed glass slide. A glass rod was rolled over the solution to spread the material uniformly over the lower four fifths of the slide. The coated slide was air dried for 4 hours and then placed in a 50% relative humidity chamber for 18 hours. The slide was then weighed to determine the weight of the coating which ranged from 2–5 mg., covering an area of 15 sq. cm. The coated slide was inserted into a slit rubber stopper and mounted over the center of a Waring Blender. The coated side faced the moving water which completely covered the coating. The blender was operated at its highest speed for 5 minutes. The slide was air dried overnight and then weighed to determine the amount of coating retained on the slide after the treatment in the Blender. The averaged results of duplicate tests are summarized in Table 1.

Table 1

| | Adhesion of Titanate Compositions | | |
|---|---|---|---|
| No. | TPT | DC-200/1000 | Retention, % |
| 1 | | 100 | 44 |
| 2 | 100 | | 80 |
| 3 | 50 | 50 | 93 |

The improvement in adhesion resulting from the hydrolysis of the titanate is quite apparent.

The 50% solutions of titanate and/or polysiloxane fluid in isooctane were mixed with a pyrethroid composition, as follows:

0.1 g. pyrethroids
0.5 g. piperonyl butoxide
0.4 g. petroleum distillate
5.0 g. 50% solution of TPT and/or DC-200/1000 in isooctane The pyrethroids-containing solutions were diluted to 10 weight-% with isooctane and coated on glass slides. The coated slides were dried, moisture cured and subjected to treatment with water in the Waring Blender, as described earlier. The amount of retained coating is summarized in Table 2, where the amount of pyrethroids indicated actually represents the sum of the pyrethroids and piperonyl butoxide.

Table 2

| | Adhesion of Pyrethroid-Titanate Compositions | | | |
|---|---|---|---|---|
| No. | TPT | DC-200/1000 | Pyrethroids | Retention, % |
| 4 | | 100 | 24 | 4 |
| 5 | 100 | | 24 | 54 |
| 6 | 50 | 50 | 24 | 46 |

Whereas the polysiloxane fluid is readily removed by the violent action of water, the adhesion-promoting effect of the titanate results in significant resistance to removal.

EXAMPLE II

A solution containing 5 weight-% non-volatiles was prepared as follows:
1.5 g. tetraisopropyl titanate (TPT)
1.5 g. DC-200/1000 dimethylpolysiloxane fluid
57.0 g. perchloroethylene The titanate-polysiloxane fluid solution was mixed with a pyrethroid composition to yield an insecticide-containing solution which was compared with an additive-free pyrethroid composition for insecticidal behavior. The components of the test compositions were as follows:

|  | Insecticide Solution | |
|---|---|---|
|  | IIA | IIB |
| Pyrethroids | 0.1 | 0.1 |
| Piperonyl butoxide | 0.5 | 0.5 |
| Petroleum distillate | 0.4 | 0.4 |
| TPT | 2.45 | — |
| DC-200/1000 | 2.45 | — |
| Perchloroethylene | 94.1 | 99.0 |

A disposable plastic syringe was used to place the test solution on a 4×4 inch glass panel. The solution was uniformly spread over the panel with the tip of the syringe. The treated panels were conditioned for 24 hours in a chamber at 78° F. and 42% relative humidity. Ten adult German cockroaches, *Blattella germanica* (Linnaeus), were exposed to the 1 day residue for 24 hours under a 100×15 mm. petri dish. The test was conducted in duplicate. The same treated panels were reexposed to cockroaches after 3, 7 and 10 days.

The percent mortality of cockroaches exposed to the treated glass panels is summarized below:

|  | Insecticide Solution | |
|---|---|---|
| Residue Age | IIA | IIB |
| 1 day | 100 | 100 |
| 3 days | 90 | 100 |
| 7 days | 55 | 15 |
| 10 days | 20 | 0 |

The residue from the control insecticide solution IIB killed 15% of the exposed cockroaches after 7 days while the residue from insecticide solution IIA, containing the titanate and polysiloxane fluid, killed 55% of the exposed cockroaches after 7 days and 20% after 10 days.

EXAMPLE III

A solution containing 50 weight-% of non-volatiles was prepared as follows:
15 g. tetraisopropyl titanate (TPT)
15 g. DC-550 methylphenylpolysiloxane fluid with 50 mole-% phenyl groups and a viscosity of 115 centistokes at 25° C.
30 g. perchloroethylene The titanate-polysiloxane fluid solution was mixed with a pyrethroid composition to yield an insecticide-containing solution which was compared with an additive-free pyrethroid composition for insecticidal behavior. The components of the test composition were as follows:

|  | Insecticide Solution | | | |
|---|---|---|---|---|
|  | IIIA | IIIB | IIIC | IIID |
| Pyrethroids | 0.1 | 0.1 | 0.1 | 0.1 |
| Piperonyl butoxide | 0.5 | 0.5 | 0.5 | 0.5 |
| Petroleum distillate | 0.4 | 0.4 | 0.4 | 0.4 |
| TPT | 2.5 | 0.5 | 0.25 | — |
| DC-550 | 2.5 | 0.5 | 0.25 | — |
| Perchloroethylene | 94.0 | 98.0 | 98.5 | 99.0 |

The insecticidal properties of solutions IIIA, IIIB, IIIC and IIID were evaluated using adult cockroaches as the test species and glass as the test surface, as described in Example II. The treated glass panels were exposed, in duplicate, to cockroaches after 1, 3, 7 and 10 days.

The percent mortality of cockroaches exposed to the treated glass panels is summarized below:

|  | Insecticide Solution | | | |
|---|---|---|---|---|
| Residue Age | IIIA | IIIB | IIIC | IIID |
| 1 day | 60 | 100 | 100 | 100 |
| 3 days | 45 | 100 | 100 | 100 |
| 7 days | 5 | 80 | 100 | 15 |
| 10 days | 0 | 0 | 45 | 0 |

The residue from the control insecticide solution IIID killed 15% of the exposed cockroaches after 7 days and was ineffective after 10 days while the residue from insecticide solution IIIC, containing 0.5% of the titanate-polysiloxane fluid mixture killed 100% of the exposed cockroaches after 7 days and 45% after 10 days. When the concentration of the titanate-polysiloxane fluid mixture in the solution was increased to 1.0%, as in solution IIIB, the release of the insecticide was retarded so that after 7 days cockroach mortality was 80% and after 10 days the release was insufficient to kill cockroaches. When the titanate-polysiloxane fluid concentration was increased to 5%, as in solution IIIA, insecticide release was so greatly retarded that only partial kills were obtained from the beginning of the test period.

EXAMPLE IV

A solution containing 50 weight-% non-volatiles was prepared as follows:
30 g. tetraisopropyl titanate (TPT)
30 g. perchloroethylene The titanate solution was mixed with S-(1,2-dicarbethoxyethyl) 0,0-dimethyl dithiophosphate (Malathion) to yield an insecticide-containing solution which was compared with an additive-free Malathion composition for insecticidal behavior. The components of the test compositions were as follows:

|  | Insecticide Solution | |
|---|---|---|
|  | IVA | IVB |
| Halathion | 0.5 | 0.5 |
| TPT | 2.5 | — |
| Perchloroethylene | 2.5 | — |
| Isopropyl alcohol | 94.5 | 99.5 |

The test compositions were applied to upper and lower leaf surfaces of potted lima bean plants with a DeVilbiss atomizer from a distance of 30.5 millimeters. There were two plants per pot, with leaves approximately 50–60 mm. wide and 70–80 mm. long. A 3.2 ml. application was sprayed evenly over the two potted plants at 3 psi pressure. The treated plants were kept in a chamber at 80° F. and 55% relative humidity. After 12 days, the treated plants were sprayed with one-half inch of tap water from a hose end sprayette #4 nozzle held at a distance of 18 inches for a period of 5–10 minutes. On the 14th day two leaves were removed from the sprayed potted plants and exposed to ten Mexican bean beetle larvae (late second instar) for 48 hours.

The leaves which had been treated with insecticide solution IVA, containing the titanate, killed 100% of the exposed larvae while the leaves which had been treated with the control insecticide IVB killed only 40% of the exposed larvae.

EXAMPLE V

The titanate solution of Example IV was mixed with Malathion to yield an insecticide-containing solution which was compared with an additive-free Malathion composition for insecticidal behavior. The components of the test compositions were as follows:

|  | Insecticide Solution | |
|---|---|---|
|  | VA | VB |
| Malathion | 0.25 | 0.25 |
| TPT | 2.5 | — |
| Perchloroethylene | 2.5 | — |
| Isopropyl alcohol | 94.75 | 99.75 |

The insecticidal properties of solutions VA and VB were evaluated using Mexican bean beetles larvae on potted lima bean plants, as described in Example IV. The treated plants were sprayed with water after 12 days and on the 14th day two leaves were removed from the plants and exposed to the larvae for 48 hours.

The leaves which had been treated with insecticide solution VA, containing the titanate, killed 75% of the exposed larvae while the leaves which had been treated with the control insecticide solution VB killed 0% of the exposed larvae.

EXAMPLE VI

The importance of adhesion was clearly shown when a 50% solution of DC-200/1000 dimethylpolysiloxane fluid in perchloroethylene was mixed with Malathion and sprayed on potted lima bean plants. The components of the test compositions were as follows:

|  | Insecticide Solution VI | |
|---|---|---|
|  | VIA | VIB |
| Malathion | 0.25 | 0.25 |
| DC-200/1000 | 2.5 | — |
| Perchloroethylene | 2.5 | — |
| Isopropyl alcohol | 94.75 | 99.75 |

The test compositions were applied to the leaves of potted lima bean plants, as described in Example IV. The treated plants were sprayed with water after 12 days and on the 14th day two leaves were removed from the plants and exposed to ten Mexican bean beetle larvae for 48 hours.

The leaves which had been treated with insecticide solution VIA, containing the polysiloxane fluid, killed only 20% of the exposed larvae, not much more effective than the leaves which had been treated with control insecticide solution VIB which killed 0% of the exposed leaves.

What is claimed is:

1. A composition consisting essentially of (a) a hydrolyzable titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines, and (b) an insecticide, said composition being capable of forming a polymeric coating.

2. A process for providing a substrate containing active hydrogen atoms with an adherent controlled release pesticide which comprises applying the composition of claim 1 to said substrate and exposing the coated substrate to atmospheric moisture.

3. A composition consisting essentially of (a) a hydrolyzable organic titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines, (b) a non-volatile, non-reactive hydrocarbon oil or organopolysiloxane, and (c) an insecticide, said composition being capable of forming a polymeric coating.

4. A composition consisting essentially of (a) a hydrolyzable organic titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines, (b) an insecticide, and (c) a volatile diluent selected from the group consisting of aliphatic or aromatic hydrocarbons, halogenated hydrocarbons, organopolysiloxane fluids, alkanols and water, said composition being capable of forming a polymeric coating.

5. A composition consisting essentially of (a) a hydrolyzable organic titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines, (b) a non-volatile, non-reactive hydrocarbon oil or organopolysiloxane, (c) an insecticide, and (d) a volatile diluent selected from the group consisting of aliphatic or aromatic hydrocarbons, halogenated hydrocarbons, organopolysiloxane fluids, alkanols and water, said composition being capable of forming a polymeric coating.

6. A process for providing a substrate containing active hydrogen atoms with an adherent controlled release pesticide which comprises applying the composition of claim 3 to said substrate and exposing the coated substrate to atmospheric moisture.

7. A process for providing a substrate containing active hydrogen atoms with an adherent controlled release pesticide which comprises applying the composition of claim 4 to said substrate and exposing the coated substrate to atmospheric moisture.

8. A process for providing a substrate containing active hydrogen atoms with an adherent controlled release pesticide which comprises applying the composition of claim 5 to said substrate and exposing the coated substrate to atmospheric moisture.

9. A process as defined in claim 2 wherein said substrate is a plant.

10. A process as defined in claim 2 wherein said substrate is an animal.

11. A process as defined in claim 2 wherein said substrate is the surface of a structure.

* * * * *